United States Patent [19]
Rivin et al.

[11] Patent Number: 5,726,068
[45] Date of Patent: Mar. 10, 1998

[54] DIFFUSIVE SAMPLER SYSTEM FOR DETERMINING CHEMICAL VAPOR LEVELS

[75] Inventors: Donald Rivin, Natick; Cyrus E. Kendrick, Stow; Martin Katz, Wellesley, all of Mass.

[73] Assignee: The United States of America as represented by the Secretary of the Army, Washington, D.C.

[21] Appl. No.: 605,230

[22] Filed: Jan. 24, 1996

[51] Int. Cl.$^6$ .................................................. G01N 21/75
[52] U.S. Cl. .......................... 436/167; 422/61; 422/87; 422/88
[58] Field of Search .................. 436/167; 422/86–88, 422/61

[56] References Cited

U.S. PATENT DOCUMENTS

| | | |
|---|---|---|
| 3,992,153 | 11/1976 | Ferber et al. |
| 4,208,912 | 6/1980 | Baldeck .................................. 422/88 |
| 4,235,097 | 11/1980 | Kring et al. |
| 4,258,000 | 3/1981 | Obermayer |
| 4,327,575 | 5/1982 | Locker |
| 4,678,690 | 7/1987 | Hamano et al. .................... 422/87 |
| 4,680,165 | 7/1987 | Vo-Dinh .............................. 422/88 |
| 4,913,881 | 4/1990 | Evers .................................. 422/56 |
| 5,110,551 | 5/1992 | Michal ............................... 422/58 |
| 5,171,536 | 12/1992 | Evers .................................. 422/88 |
| 5,364,593 | 11/1994 | Mihaylov et al. ................. 422/87 |
| 5,490,971 | 2/1996 | Giffard et al. .................... 422/88 |

*Primary Examiner*—Lyle A. Alexander
*Attorney, Agent, or Firm*—Vincent J. Ranucci

[57] ABSTRACT

A diffusive sampler for effectively determining chemical vapor levels, the sampler having a thin pouch-like container made up of an impermeable back sheet and a selectively permeable front membrane attached thereto along its peripheral edges. The front membrane is made of a material capable of passing preselected vapors therethrough and for preventing other preselected vapors from passing therethrough and preferably has substantially the same permeation rate as human skin. Located within the pouch-like container is an adsorbent substance for adsorbing the chemical vapor and for providing information with respect to the chemical vapor levels adsorbed thereby. In use a plurality of the samplers are adhered to the skin of an individual wearing a protective garment to establish the effectiveness of the garment when subjected to specific chemical vapors.

15 Claims, 1 Drawing Sheet

DIFFUSIVE SAMPLER SYSTEM FOR DETERMINING CHEMICAL VAPOR LEVELS

STATEMENT OF GOVERNMENT INTEREST

The invention described herein may be manufactured and used by and for the Government for governmental purposes without the payment of any royalty thereon.

FIELD OF THE INVENTION

The present invention relates generally to chemical vapor detecting devices and, more particularly, to a small, low-weight diffusive sampler system which can be readily utilized for determining chemical vapor levels beneath a chemical protection garment.

BACKGROUND OF THE INVENTION

In today's environment toxic vapors pose a significant health hazard to personnel both in the work place and other such environments. One method to protect personnel from the exposure to toxic vapors is to protect the workers by the utilization of a protective garment which prevents such vapors from causing damage to personnel working in such a toxic vapor environment. Even with the utilization of such protective garments, however, there are instances when it is highly desirable to study both the effectiveness of such garments and also to study the effects of such toxic vapors on the individuals wearing the garments. Furthermore, there are instances in which individuals are located in an environmental conditions where the possibility of coming in contact with toxic vapors is a reality although not a usual occurrence. Therefore, it is essential to monitor the surrounding environment in which an individual is located both outside the protective garment as well as within the protective garment.

The monitoring of vapors can be performed by many systems. For example, the bubbling of a known quantity of air through an absorbing solution and measuring the concentrations thereof; passing a known quantity of gas through a column having an absorbent which changes color based upon the gas; adsorbing gas onto an activated material and measuring the quantity of adsorbed gas over a known time; adsorbing gas into a solution and measuring its concentration; measuring the change in the electrical properties of a solid state device after contamination; and measuring the characteristics of color developed in a tube filled with a chromophore and using a diffusion-barrier based passive sampler with a subsequent analysis for determining the gaseous content.

Devices which incorporate the above methods of determining vapor content generally are incorporated within a sampler which is bulky and does not fit comfortably under clothing such as a protective garment since its intended use is to be placed on top of clothing rather than beneath. In addition, many such systems use a colorimetric system for analysis which does not have the sensitivity required in ascertaining the small amounts of vapor which may penetrate a protective garment. Furthermore, systems in use today do not have the sensitivity required for testing at a number of various locations on a body being subjected to a toxic vapor environment.

It is therefore an object of this invention to provide a diffusive sampler for determining extremely small chemical vapor levels.

It is another object of this invention to provide a diffusive sampler which incorporates therein a small, thin, pouch-like container for holding an adsorbent material.

It is still another object of this invention to provide a diffusive sampler designed to replicate the absorbent characteristics of skin.

It is a further object of this invention to provide a diffusive sampler system for determining chemical vapor levels which can be adhered to a body beneath a protective garment with minimal alteration of the airflow beneath the garment.

It is still a further object of this invention to provide a diffusive sampler system for determining chemical vapor levels which incorporate therein a plurality of samplers utilized at a plurality of positions on a body in order to analyze the vapor levels at preselected positions on the body in order to study the effectiveness of a protective garment.

It is an even further object of this invention to provide a diffusive sampler system for determining chemical vapor levels which is insensitive to the direction of flow and convectional flow effects of the vapor.

It is an additional object of this invention to provide a diffusive sampler system for determining chemical vapor levels which is readily affixed to any part of the human anatomy.

SUMMARY OF THE INVENTION

The present invention overcomes the problems associated with vapor level detection devices of the past and which can be easily utilized in conjunction with protective garments. The sampler of this invention includes an inexpensive, Small, thin and light weight pouch that can be affixed to any part of the human anatomy, to clothing or to any structure to ascertain the level of chemical vapor at the sampler. Because of the thinness, small size and low weight, the sampler can be easily affixed to a desired site with minimal alteration of the airflow beneath a protective garment, if utilized therewith.

In addition, the utilization of a series of such samplers at various sites on the human body and an analysis of the vapors detected thereby can provide a procedure in which the effectiveness of a protective garment can be quickly ascertained and studied. During such a test procedure samplers are attached to the skin at selected sites. The human subject is clothed in a chemical protective garment and then exposed to various chemical agents or simulants. After a predetermined time of exposure, the detector contained within the sampler is analyzed for the level of chemical agent simulant that may have passed through the chemical protective clothing. In this way relative chemical agent protection can be determined.

Human skin functions as an air-impermeable diffusion membrane, such that when a person is exposed percutaneously to a vapor under variable flow direction and velocity, only a small fraction of the vapor dose penetrates into the body. The extent of penetration of a given vapor depends on the permeation resistance of the skin which is mainly independent of variations in flow and vapor concentration, and the aerodynamic surface resistance which is a function of flow velocity.

The diffusive sampler of this invention incorporates a membrane therein which has similar permeation resistance to skin, so that when placed on the body under a protective garment it exhibits the same permeation rate as does skin. This equivalence can be extended to matching the resistance of skin towards a toxic vapor so that the diffusive sampler of the present invention can be used to detect a non-toxic vapor such that the rate of adsorption by the sampler is similar to the rate of absorption of the toxic vapor by skin under the same conditions of exposure. Thus, the effectiveness of a protective garment can be determined reliably by exposing protected individuals to the non-toxic vapor under appropriate exposure scenarios.

Furthermore, the membrane utilized in this invention can be chosen also for its selective barrier properties against potential contaminants which could interfere in the subsequent analysis of the contained adsorbent. For example, an hydrocarbon polymer film such as polyethylene is a good barrier against permeation of water vapor, and polar organic molecules present in sweat.

The fact that the sampler is of small size and low weight makes it easily attachable to various parts of a human body. This enables the diffusive sampler system of this invention to have widespread application wherever there is a requirement for the detection of chemical vapors on a quantitative or qualitative basis. A direct quantitative relationship between adsorption by the sampler and agent absorption by the skin can be established independently. Because of the design of the sampler of this invention the results are relatively insensitive to the direction of flow and convectional flow effects of the gaseous vapor.

More specifically the sampler of the present invention includes a small, thin pouch-like container made up of an impermeable and flexible sheet material coated with a thin thermoplastic film for lamination. This sheet is thermally bonded or attached by an adhesive at its edges to a permeable membrane, film or screen selected to produce the desired permeation rate. The surface area of the exposed permeable film or screen is established in the design of the sampler and the permeable membrane is chosen to duplicate the absorption characteristics of the skin for the vapor of interest.

Contained within the sealed pouch is an adsorbent material designed to adsorb the chemical vapors of interest. After subjecting the sampler to a gaseous vapor, the adsorbent detector is removed and the bound vapor is desorbed by thermal or chemical means and analyzed using conventional analytical techniques. The choice of the adsorbent and the permeable film can vary within the scope of the invention and is selected for the particular gaseous vapor to be adsorbed during use. The sampler is attached to the body or surrounding clothing with an adhesive tape of the double back variety.

For a better understanding of the present invention, together with other and further objects, reference is made to the following description taken in conjunction with the accompanying drawings, and its scope will be pointed out in the appended claims.

DETAILED DESCRIPTION OF THE PREFERRED EMBODIMENTS

Figure 1:
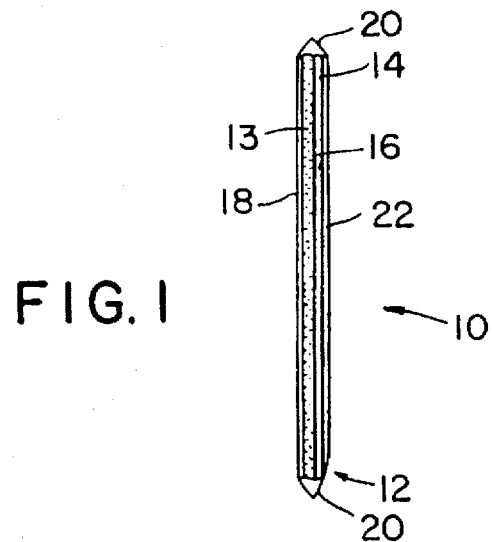
FIG. 1 is an enlarged cross-sectional view of the diffusive sampler of this invention.
Figure 2:
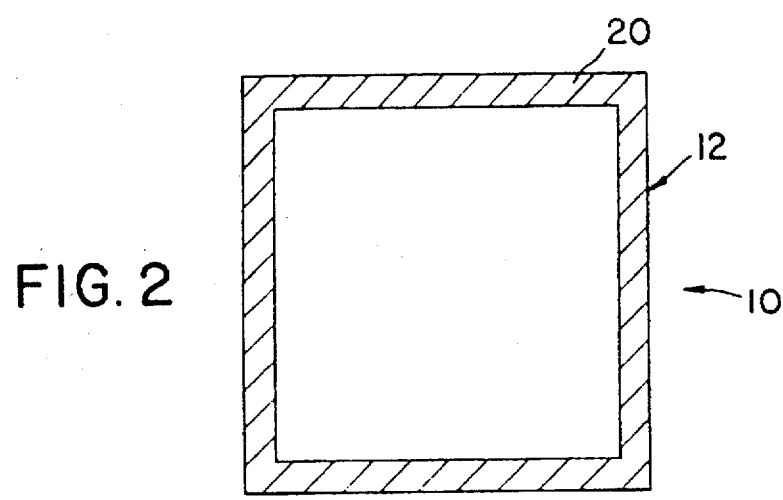
FIG. 2 is an enlarged front view of the diffusive sampler of this invention.

Referring to FIGS. 1 and 2 of the drawings, the diffusive sampler 10 of this invention is made up of a thin pouch-like container 12 having an adsorbent material 13 situated therein.

More specifically, pouch-like container 12 has an impermeable and flexible back sheet 14 made of any suitable material such as aluminum foil coated with a thin polyethylene film 16. This flexible sheet is preferably approximately 0.005 inches in thickness. The front of container 12 is in the form of a permeable film 18 made of a membrane or film 18 of known vapor transmission. For example, membrane 18 can have the same flow dependence as skin under similar flow conditions. Film 18 can be made of a high density polyethylene (HDPE) of known vapor transmission and be approximately 0.001 inches thick. Preferably, membrane 18 duplicates the absorption characteristics of human skin.

Film 18 and sheet 14 are attached together at its edges 20 by thermal bonding or any other suitable sealing procedure or adhesive. By providing sealing edges of approximately ⅛ inch width, the surface area of the exposed permeable membrane or film is established.

Although various types of adsorbent material can be used with this invention, an example of an adsorbent material 13 which can be used with this invention is 50 milligrams of TENAX TA,® an adsorbent capable of adsorbing many organic vapors, including methyl salicylate vapor (MeS). Furthermore, an adhesive 22, in the form of a conventional adhesive tape of the double backed variety, is affixed to the rear surface of flexible back sheet 14. This tape can be, for example, 3M #1509 double coated medical tape.

Overall, a preferred embodiment of the diffusive sampler 10 has an outer dimension of 0.5–2 inches×0.5–2 inches, a large permeable membrane area anal an overall thickness of approximately 0.055 inches. Although these dimensions may vary within the scope of this invention, it is essential that the dimensions be maintained such that the diffusive sampler can be readily attached to the skin of an individual wearing a protective garment without obstructing air flow therein, without being damaged by the protective garment and without restricting the movement of the individual.

To better understand the concepts involved with the present invention, it must be first recognized that human skin functions as an air-impermeable diffusion membrane. In other words, when a person is exposed percutaneously to a vapor under variable flow direction and velocity, only a small fraction of the vapor dose penetrates into the body. The extent of penetration of a given vapor depends on the permeation resistance of the skin, which is mainly independent of variations in flow and vapor concentration, and the aerodynamic surface resistance which is a function of flow velocity.

A main feature of the diffusive sampler system of this invention is that it relies upon a membrane 18 having a similar permeation resistance to skin, so that when placed on the body under a protective garment it exhibits the same permeation rate as does skin. This equivalence can be extended to matching the resistance of skin towards a toxic vapor. In use, however, it is desirable to utilize a membrane 18 which is effective with respect to a non-toxic vapor which may or may not have properties similar to a toxic vapor. However, the sampler membrane 18 must be selected so that uptake of non-toxic vapor by sampler 10 is similar to uptake of toxic vapor by skin under the same exposure conditions. More specifically, permeation of a non-toxic vapor through membrane 18 can be correlated with the permeation of a toxic vapor through skin for the same conditions of exposure. Account can be taken of different skin absorption rates in different regions of the body. Thus, a garment's protection against a toxic vapor can be evaluated with the diffusive sampler 10 of this invention by exposing individuals clothed with the protective garment to the non-toxic vapor under appropriate exposure scenarios.

Furthermore, membrane 18 Should be chosen for its selective barrier properties against potential contaminants which could interfere in the subsequent analysis of the contained adsorbent 13. For example, an hydrocarbon polymer film such as polyethylene is a good barrier against permeation of water vapor, and polar organic molecules present in sweat.

Figure 3:
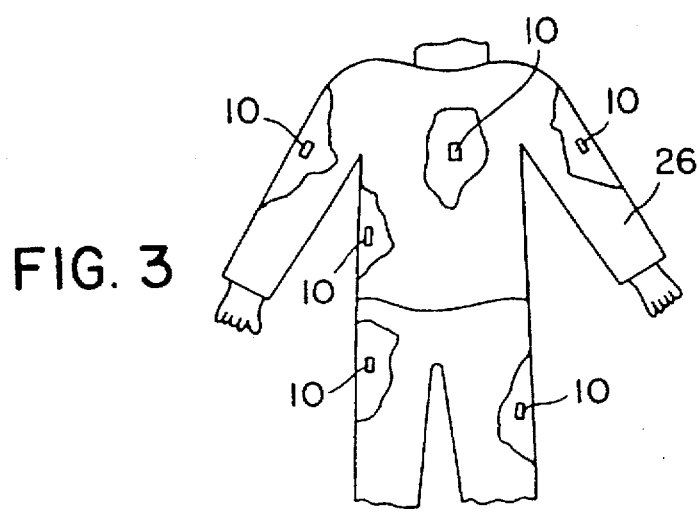
FIG. 3 is a pictorial illustration of the diffusive sampler of this invention attached at various locations of the body beneath a protective garment worn by an individual.

In order to test the effectiveness of a protective garment in a chemical vapor environment, a plurality of samplers 10, as shown in FIG. 3 of the drawings, are adhered at various sites on the human body, preferably beneath a protective garment 26. Rapid analysis of the vapors detected can provide a procedure in which the effectiveness of a protective garment can be quickly ascertained and studied.

During such a test procedure samplers are attached to the skin at preselected sites. The human subject is clothed in a chemical protective garment 26 and then exposed to various vapors of interest. After a predetermined time of exposure, the adsorbent material 13, contained within the sampler 10, is analyzed for the level of chemical agent simulant that may have passed through the chemical protective garment or clothing. In this way relative chemical agent protection can be accurately determined.

The design of sampler 10, that is, being of small size, low weight, and easily attachable to various parts of a human body enables the diffusive sampler system of this invention to have wide spread application wherever there is a requirement for the detection of chemical vapors on a quantitative or qualitative basis. A direct quantitative relationship between non-toxic vapor adsorption by the sampler and agent absorption by the skin can be established independently. Furthermore, sampler 10 of this invention provides results that are relatively insensitive to the direction of flow and convectional flow effects of a gaseous vapor.

After subjecting sampler 10 to a gaseous vapor, the adsorbent material or detector 13 is removed from the pouch-like container 12. The bound vapor is desorbed by conventional thermal or chemical means and analyzed using conventional analytical techniques. The choice of the adsorbent material 13 and the permeable film or membrane 18 can vary within the scope of the invention and is selected for the particular gaseous vapor to be adsorbed during use.

Although the invention has been described with reference to particular embodiments, it will be understood that this invention is also capable of further and other embodiments within the spirit and scope of the appended claims.

What is claimed is:

1. A diffusive sampler for effectively determining chemical vapor levels, and for wearing under a garment to measure any vapor absorbed by skin exposed to vapor under the garment, said sampler comprising:

a container having an impermeable back sheet and a selectively permeable front membrane attached thereto along its peripheral edges;

said front membrane being made of means for passing preselected vapors therethrough and for preventing other preselected vapors from passing therethrough;

means located within said container for adsorbing said chemical vapor and for providing information with respect to said chemical vapor levels adsorbed thereby;

said vapor passing means comprising a high density polyethylene material which has substantially the same permeation resistance as human skin;

said vapor passing means being a material which has a permeation rate capable of passing a non-toxic vapor therethrough, said rate being similar to the rate of toxic vapor absorption by skin under the same conditions of exposure;

said sampler having a thickness and being affixable to a human anatomy with minimal alteration of airflow beneath said garment: and said front membrane and said back sheet being attached together along peripheral edges of said sampler along an area of approximately ⅛ inches from said edges.

2. A diffusive sampler as defined in claim 1 wherein said other preselected vapors comprise polar vapors and water vapors.

3. A diffusive sampler as defined in claim 1 wherein said container has a width of approximately 0.5 inches to 2 inches and a length of approximately 0.5 inches to 2 inches.

4. A diffusive sampler as defined in claim 3 wherein said front membrane and said back sheet are attached together along its peripheral edges along an area of approximately ⅛ inches from said edges.

5. A diffusive sampler as defined in claim 1 wherein said thickness of said sampler is approximately 0.05 inches.

6. A diffusive sampler as defined in claim 5 wherein said back sheet has means affixed thereto to removably adhere said sampler to a surface.

7. A diffusive sampler as defined in claim 6 wherein said back sheet is made of aluminum foil.

8. A method of determining the effectiveness of a protective garment in protecting an individual from chemical vapors, said method comprising the steps of:

providing a plurality of diffusive samplers, each of said samplers having a container, said container having an impermeable back sheet and a selectively permeable front membrane attached thereto, said front membrane having substantially the same permeation resistance as human skin, and means located within said container for adsorbing said chemical vapors and for providing information with respect to said chemical vapor levels adsorbed thereby;

adhering said plurality of diffusive samplers to preselected locations on the skin of an individual;

clothing said individual in a protective garment;

said samplers comprising high density polyethylene and having a thickness such that said adhering on said skin is with minimal alteration of airflow beneath said garment;

exposing said individual to said chemical vapors; and analyzing said adsorbing means in order to ascertain the presence of said chemical vapors in order to ascertain the effectiveness of said protective garment.

9. A method of determining the effectiveness of a protective garment as defined in claim 8 wherein said adsorbing means is capable of adsorbing methyl salicylate vapors.

10. A method of determining the effectiveness of a protective garment as defined in claim 8 wherein the thickness of said sampler is approximately 0.05 inches.

11. A method of determining the effectiveness of a protective garment as defined in claim 8 wherein said container has a width of approximately 0.5 inches to 2 inches and a length of approximately 0.5 inches to 2 inches.

12. A method of determining the effectiveness of a protective garment as defined in claim 11 whereto said front membrane and said back sheet are attached together along its peripheral edges along an area of approximately ⅛ inches from said edges.

13. A method of determining the effectiveness of a protective garment in protecting an individual from toxic vapor, said method comprising the steps of:

providing a plurality of diffusive samplers, each of said samplers having a container, said container having an impermeable back sheet and a selectively permeable front membrane attached thereto, said front membrane having a permeation rate towards a test vapor which is similar to the rate of absorption of said toxic vapor by human skin, and means located within said container for adsorbing said test vapor and for providing information with respect to said test vapor levels adsorbed thereby;

adhering said plurality of diffusive samplers to preselected locations on the skin of an individual;

clothing said individual in a protective garment;

said samplers comprising high density polyethylene and having a thickness such that said adhering on said skin is with minimal alteration of airflow beneath said garment;

exposing said individual to said test vapor; and analyzing said adsorbing means in order to ascertain the presence of said test vapor in order to ascertain the effectiveness of said protective garment with respect to said toxic vapor.

14. A method of determining the effectiveness of a protective garment as defined in claim 13 wherein said front membrane acts as a barrier against contaminants which would interfere with said analyzing step.

15. A method of determining the effectiveness of a protective garment as defined in claim 13 further comprising the step of establishing a direct quantitative relationship between adsorption of said test vapor by said sampler and absorption of said toxic vapor by said skin.

* * * * *